United States Patent
Clapot et al.

[11] 3,990,883
[45] Nov. 9, 1976

[54] N-(1-CARBOXY-3-METHYLTHIO)PROPYL UREA DERIVATIVES AND COMPOSITIONS HAVING PLANT-GROWTH REGULATING PROPERTIES

[75] Inventors: Claude Clapot, Oullins; Jean Vial, Tassin; Louis Dumont, Chaponost, all of France

[73] Assignee: PEPRO. Societe pour le Development et la Vente de Specialitis Chimiques, Lyon, France

[22] Filed: May 22, 1974

[21] Appl. No.: 472,471

[30] Foreign Application Priority Data
May 22, 1973 France .............. 73.19579

[52] U.S. Cl. ............ 71/98; 71/72; 71/76; 71/92; 260/294.8 R; 260/294.8 H; 260/309.5; 260/438.1; 260/465 D; 260/470; 260/515 R; 260/515 A; 260/515 M
[51] Int. Cl.² ............................. A01N 9/12
[58] Field of Search ............... 71/98, 115, 99

[56] References Cited
UNITED STATES PATENTS

| | | | |
|---|---|---|---|
| 3,020,145 | 2/1962 | Gobeil et al. ............ | 71/115 |
| 3,340,042 | 9/1967 | Schwartz .................. | 71/98 |
| 3,671,212 | 6/1972 | Jaworski .................. | 71/98 |

FOREIGN PATENTS OR APPLICATIONS

| | | | |
|---|---|---|---|
| 782,037 | 4/1972 | Belgium ................. | 71/98 |
| 465,004 | 2/1971 | Japan .................... | 71/98 |
| 430,323 | 8/1967 | Switzerland ............. | 71/98 |

*Primary Examiner*—Glennon H. Hollrah
*Attorney, Agent, or Firm*—Browdy and Neimark

[57] ABSTRACT
Compounds corresponding to the general formulae:

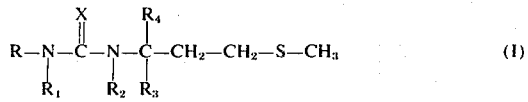

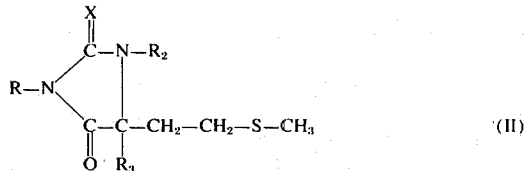

in which
R represents hydrogen, an alkyl radical, a halogenated alkyl radical, a cycloalkyl radical, an optionally substituted aryl radical, an optionally substituted aralkyl radical, an acyl radical, aroyl radical or an optionally substituted heterocycle;

$R_1$ and $R_3$, which may be the same or different, represent hydrogen, aralkyl radical containing 1 to 5 carbon atoms;

$R_2$ represents hydrogen, an alkyl radical (optionally halogenated or substituted by a hydroxyl), a formyl radical, an acyl radical, a carbamoyl radical monosubstituted or disubstituted on the nitrogen;

R and $R_2$ cannot both represent hydrogen;

$R_4$ is the carboxylic acid radical or one of its ester, amide, nitrile derivatives or a salt of an alkaline metal, alkaline-earth metal or heavier metal, in which case several molecules (1) can be associated with the metal atom;

X represents oxygen or sulphur, and their salts, especially their sulphonium salts. Such compounds are useful for modifying the growth of plants.

14 Claims, No Drawings

N-(1-CARBOXY-3-METHYLTHIO)PROPYL UREA DERIVATIVES AND COMPOSITIONS HAVING PLANT-GROWTH REGULATING PROPERTIES is

This invention relates to new hydantoin derivatives and to compositions based on methionine derivatives with plant-growth regulating properties.

The term "growth regulator" s used in its accepted sense in the French language, which corresponds to "growth substance" in Anglo-Saxon literature, the term "growth" relating to the production of living matter and not simply to the modification of the size of plants. Accordingly, growth regulators in the context of the invention are compounds which are capable of modifying the physiology of plants in different ways.

It has already been proposed (cf. Belgian Pat. 782,037) to use methionine and certain of its esters as growth regulators. Unfortunately, compounds of this kind are often not effective enough for commercial application.

The present invention relates to other compounds of methionine which correspond to the following general formulae:

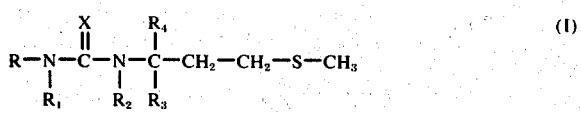

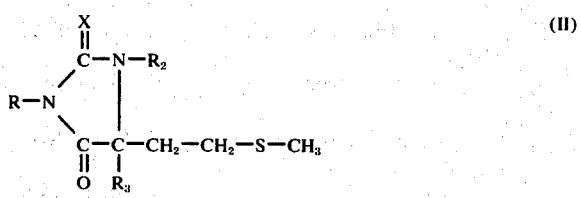

and to their salts, especially their sulphonium salts. In the above formulae:

R represents hydrogen, an alkyl radical, a halogenated alkyl radical, a cycloalkyl radical, an optionally substituted aryl radical, an optionally substituted aralkyl radical, an acyl or aroyl radical, an optionally substituted heterocycle, the alkyl portion preferably containing 1 to 5 carbon atoms;

$R_1$ and $R_3$, which may be the same or different, represent hydrogen, an alkyl radical containing 1 to 5 carbon atoms;

$R_2$ represents hydrogen, alkyl (optionally halogenated or substituted by a hydroxyl), formyl, acyl, carbamoyl monosubstituted or disubstituted on the nitrogen;

$R_4$ is the carboxylic acid radical or one of its ester, amide, nitrile derivatives or a salt of an alkali metal, alkaline-earth metal or heavier metal, in which case several molecules (I) can be associated with one metal atom;

X represents oxygen or sulphur.

Some of these compounds have already been described in the literature, although none of them has ever been described for its plant-growth regulating properties.

Of particular interest are the compounds according to the invention which correspond to the formulae:

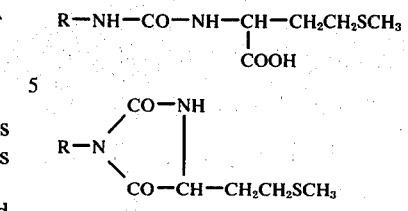

where R represents hydrogen, an alkyl radical, a halogenated alkyl radical, a cycloalkyl radical, an optionally substituted aryl radical of the formula

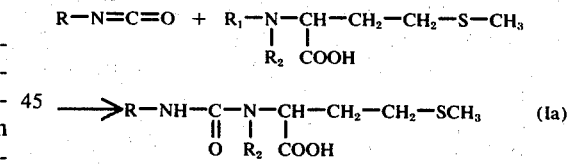

in which A represents hydrogen or halogen, B represents hydrogen, halogen, an alkyl, alkoxy, $NO_2$, CN, $CF_3$, COOR′ where R′ represents hydrogen or alkyl;

m is an integer from 0 to 5, n is an integer from 0 to 3, m and n together being at most equal to 5;

an optionally substituted aralkyl radical, an acyl radical, aroyl radical or an optionally substituted heterocycle; the alkyl part of the radicals containing from 1 to 5 carbon atoms.

The compounds according to the invention can be prepared as follows:

Compounds of formula (I), in which $R_4$ is a carboxylic acid radical COOH, are synthesized by a process of the kind commonly used for the preparation of ureas, for example by reacting an alkyl, aryl or aralkyl iso(thio) cyanate with methionine or one of its N-substituted derivatives in accordance with the following scheme:

$$R-N=C=O + R_1-N-CH-CH_2-CH_2-S-CH_3$$
$$\phantom{R-N=C=O +\ } | \phantom{-}|$$
$$\phantom{R-N=C=O +\ } R_2\ COOH$$

$$\longrightarrow R-NH-C-N-CH-CH_2-CH_2-SCH_3 \quad (Ia)$$
$$\phantom{\longrightarrow R-NH-}|| \phantom{-}| \phantom{-}|$$
$$\phantom{\longrightarrow R-NH-}O\ R_2\ COOH$$

The isocyanate, in solution in a solvent, for example dioxan, is poured slowly with vigorous stirring into an aqueous solution of dl-methionine in alkaline medium. During the introduction, the medium is cooled to maintain a temperature at most equal to 30° C. The reactants are then stirred for a few hours at room temperature. The reaction medium is filtered and the medium subsequently acidified, the temperature remaining at most equal to 10° C. The urea is precipitated. It is centrifuged, washed and dried. This urea can then be esterified or salified with alkali metals or heavier metals by conventional methods.

The following compounds were prepared by this process:

1. dl-N-phenyl-N′-(1-carboxy-3-methylthio)-propyl urea
2. the copper (II) salt of dl-N-phenyl-N′-(1-carboxy-3-methyl thio)-propyl urea
3. dl-N-(2-chlorphenyl)-N′-(1-carboxy-3-methylthio)-propyl urea 4. dl-N-(3-chlorphenyl)-N'-(1-carboxy-3-methylthio)-propyl urea
5. dl-N-(4-chlorphenyl)-N'-(1-carboxy-3-methylthio)-propyl urea
6. dl-N-(2,3-dichlorphenyl)-N'-(1-carboxy-3-methylthio)-propylurea
7. dl-N-(2,4-dichlorphenyl)-N'-(1-carboxy-3-methylthio)-propyl urea
8. dl-N-(2,5-dichlorophenyl)-N'-(1-carboxy-3-methylthio)-urea
9. dl-N-(2,6-dichlorphenyl)-N'-(1-carboxy-3-methylthio)-propyl urea
10. dl-N-(3,4-dichlorphenyl)-N'-(1-carboxy-3-methylthio)-propyl urea
11. dl-N-(3,5-dichlorphenyl)-N'-(1-carboxy-3-methylthio)-propyl urea
12. copper (II) salt of N-(3,5-dichlorphenyl)-N'-(1-carboxy-3-methylthio)-propylurea
13. dl-N-(4-nitrophenyl)-N'-(1-carboxy-3-methylthio)propyl urea
14. dl-N-(4-cyanophenyl)-N'-(1-carboxy-3-methylthio)propyl urea
15. dl-N-(3-trifluormethylphenyl)-N'-(1-carboxy-3-methylthio)-propyl urea
16. dl-N-(2-methylphenyl)-N'-(1-carboxy-3-methylthio)-propyl urea
17. dl-N-(3-methylphenyl)-N'-(1-carboxy-3-methylthio)-propyl urea
18. dl-N-(4-methylphenyl)-N'-(1-carboxy-3-methylthio)-propyl urea
19. dl-N-(4-isopropylphenyl)-N'-(1-carboxy-3-methylthio)-propyl urea
20. dl-N-(4-tert.-butylphenyl)-N'-(1-carboxy-3-methylthio)-propyl urea
21. dl-N-(4-methoxyphenyl)-N'-(1-carboxy-3-methylthio)-propyl urea
22. dl-N-(1-naphthyl)-N'-(1-carboxy-3-methylthio)-propyl urea
23. dl-N-(styryl)-N'-(1-carboxy-3-methylthio)-propyl urea
24. dl-N-(2,4-dichlorbenzyl)-N'-(1-carboxy-3-methylthio)-propyl urea
25. dl-N-(cyclohexyl)-N'-(1-carboxy-3-methylthio)-propyl urea
26. dl-N-(1-carboxy-3-methyl thio)propyl urea.

As to compounds of formula (I) in which $R_4$ is a nitrile radical, they are synthetizised by a process of the kind commonly used, by reacting an alkyl-, aryl or aralkyl (thio) isocyanate with 2-amino 4 methylthiobutyronitrile in accordance with the following scheme:

63 - (DL) N-methyl - N' - (I-cyano, 3 methylthio)-propylurea
64 - (DL) N-phenyl-N' - (I-cyano, 3 methylthio) propylurea
65 - (DL) N 3,5 dichlorophenyl-N' (I-cyano, 3 methylthio)propylurea
66 - (DL) N 3,4 dichlorophenyl-N' (I-cyano, 3 methylthio) propylurea
67 - (DL) N- (αnaphthyl) N' (I-cyano, 3 methylthio) propylurea The compounds of formula II can be obtained in two stages by two separate methods.

The first method comprises cyclising a urea (I) simply by boiling for several hours in hydrochloric acid. The hydantoin precipitates on cooling, the precipitate being washed and dried.

The following compounds were obtained by this process:

27. 3-phenyl-5-(methylthioethyl)hydantoin
28. 3-(2-chlorphenyl)-5-(methylthioethyl)-hydantoin
29. 3-(3-chlorphenyl)-5-(methylthioethyl)-hydantoin
30. 3-(4-chlorphenyl)-5-(methylthioethyl)-hydantoin
31. 3-(2,3-dichlorphenyl)-5-(methylthioethyl)-hydantoin
32. 3-(2,4-dichlorphenyl)-5-(methylthioethyl)-hydantoin
33. 3-(2,5-dichlorphenyl)-5-(methylthioethyl)-hydantoin
34. 3-(2,6-dichlorphenyl)-5-(methylthioethyl)-hydantoin
35. 3-(3,4-dichlorphenyl)-5-(methylthioethyl)-hydantoin
36. 3-(3,5-dichlorphenyl)-5-(methylthioethyl)-hydantoin
37. 3-(4-nitrophenyl)-5-(methylthioethyl)-hydantoin
38. 3-(4-carboxyphenyl)-5-(methylthioethyl)-hydantoin
39. 3-(3-trifluormethylphenyl)-5-(methylthioethyl)-hydantoin
40. 3-(2-methylphenyl)-5-(methylthioethyl)-hydantoin
41. 3-(3-methylphenyl)-5-(methylthioethyl)-hydantoin
42. 3-(4-methylphenyl)-5-(methylthioethyl)-hydantoin
43. 3-(4-isopropylphenyl)-5-(methylthioethyl)-hydantoin
44. 3-(4-tert.-butylphenyl)-5-(methylthioethyl)-

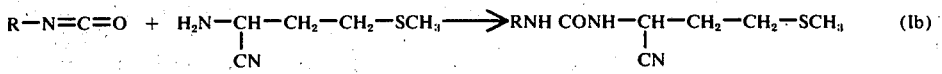

The isocyanate, in solution in an inert solvent, for example benzene, is poured dropwise with stirring to a solution in benzene of 2-amino 4-methylthiobutyronitrile, the medium being cooled to maintain a temperature at most equal to 30° C.

After about half an hour, the desired product begins to precipitate. The, when it is completely cooled, it is filtered, centrifugated, washed and dried.

The following compounds were prepared by this process:

hydantoin
45. 3-(4-methoxyphenyl)-5-(methylthioethyl)-hydantoin
46. 3-(1-naphthyl)-5-(methylthioethyl)-hydantoin
47. 3-methyl-5-(methylthioethyl)-hydantoin
48. 3-(2,4-dichlorbenzyl)-5-(methylthioethyl)-hydantoin
49. 3-cyclohexyl-5-(methylthioethyl)-hydantoin
50. 5-(methylthioethyl)-hydantoin In a second method for synthesising the compounds of formula (II), where $R_2$ is hydrogen, an amine is reacted with an isocyanate derivative of a methionine ester in accordance with the following scheme:

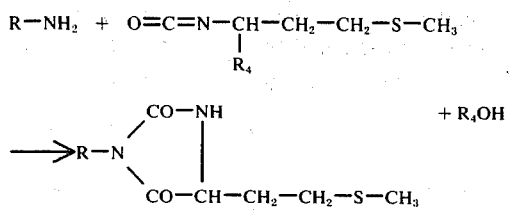

The isocyanate is slowly added to an organic solution, for example a pyridine solution, of the amine. The reaction takes place spontaneously, being accompanied by the elimination of alcohol. The reaction medium is then concentrated to dryness under reduced pressure and the residue purified by fractional crystallisation.

The following compounds were obtained by this process:
51. 3-carboxyethyl-5-methylthioethyl hydantoin
52. 3-furfuryl-5-methylthioethyl hydantoin
53. 3-(3-pyridyl)-5-methylthioethyl hydantoin
54. 3-(4-pyridyl)-5-methylthioethyl hydantoin The compounds of general formula (II), in which $R_2$ is a substituent, can be obtained by reacting a previously obtained compound (II) with a reactant of the formula $R_2Z$, in which Z is a mineral or organic anion, under heat in the presence of an acid acceptor:

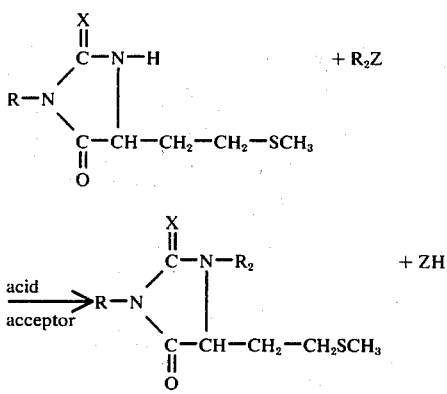

The following compounds were obtained by this process:
55. 1-methyl-3-phenyl-5-methylthioethyl hydantoin
56. 1-acetyl-3-phenyl-5-methylthioethyl hydantoin
57. 1-(3-chlorethoxycarbonyl)-3-phenyl-5-methylthioethyl hydantoin
58. 1-(n-propylcarbamoyl)-3-phenyl-5-methylthioethyl hydantoin.

The invention also relates to the sulphonium salts of the compounds of formula (II). These salts can be obtained by mixing a compound of formula (II) with a compound of the formula R'Y, in which R' is a $C_1$–$C_5$-alkyl whilst Y is a halogen atom, with stirring for 2 to 10 hours at ambient temperature in a polar solvent, for example acetone, and in the absence of an acid acceptor. The reaction takes place in accordance with the following scheme:

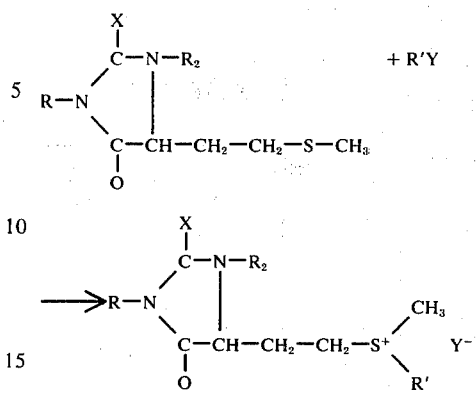

The following compounds were obtained by this process:
59. dimethyl-(3-phenylhydantoinyl)-ethylsulphonium iodide
60. dimethyl-(3-phenylhydantoinyl)-ethylsulphonium bromide
61. dimethyl-3-(3,5-dichlorphenyl)-hydantoinyl ethylsulphonium iodide
62. dimethyl-3-(3,5-dichlorphenyl)-hydantoinyl ethylsulphonium bromide.

The following Examples illustrate the preparation of the compounds according to the invention and their plant-growth regulating properties.

Examples 1 to 26: Preparation of compounds of formula (I)

EXAMPLE 1

Preparation of N-phenyl-N'-(1-carboxy-3-methyl thio)-propyl urea

A solution of 119 g (1 mole) of phenylisocyanate in 100 ml of dioxan is added dropwise to an aqueous solution of dl-methionine (149 g, 1 mole) in the presence of one equivalent of soda. On completion of the addition, the reactants are stirred at ambient temperature for 2 hours. The symmetrical diphenyl urea (secondary reaction product) is eliminated by filtration. The medium is then reacidified to pH 2, the temperature not exceeding 10° C. The N-phenyl-N'-(1-carboxy-3-methylthio)-propyl urea precipitates. It is centrifuged, washed and dried.

Yield: 72% (of product recrystallised from methanol)

Melting point: 139° C

Centesimal analysis for $C_{12}H_{16}N_2O_3S = 268$

|  | C % | H % | N % |
|---|---|---|---|
| calculated | 53.73 | 5.97 | 10.45 |
| found | 53.82 | 5.98 | 10.47 |

EXAMPLE 2

Preparation of the copper (II) salt of N-phenyl-N'-(1-carboxy-3-methyl thio)-propyl urea 20 g (0.075 mole) of N-phenyl-N'-(1-carboxy-3-methyl thio)-propyl urea are dissolved in a normal alkaline soda solution. A solution of 9.4 g (0.075 mole) of copper (II) sulphate containing one half-equivalent of the salt is then added to the resulting solution. The copper salt of the urea precipitates. It is centrifuged, washed with water and dried.
Yield: 60%
Melting point: above 300° C
Centesimal analysis for $C_{24}H_{30}N_4O_6S_2Cu$

|  | C % | H % | N % | Cu % |
|---|---|---|---|---|
| calculated | 48.20 | 5.02 | 9.37 | 10.62 |
| found | 48.16 | 5.10 | 9.23 | 10.49 |

This salt dissolves in ammonia to form a blue-coloured solution.

EXAMPLES 3 to 11 and 13 to 26

The procedure is as in Example 1. The characteristics of the compounds obtained and their yields are set out in the following Table.

$$R-NH-CO-NH-\underset{\underset{COOH}{|}}{CH}-CH_2CH_2SCH_3$$

| Compound No. | R | Structure obtained — Empirical formula | MW | Physical constants | Yield | Centesimal analysis | | | |
|---|---|---|---|---|---|---|---|---|---|
|  |  |  |  |  |  |  | C % | H % | N % | Cu % |
| 1 | phenyl | $C_{12}H_{16}N_2O_3S$ | 268 | m.p. 138.8° C | 72 % | C: 53.73 / F: 53.82 | 5.97 / 5.98 | 10.45 / 10.47 |  |
| 2 | phenyl — Cu (II) salt | $C_{24}H_{30}N_4O_6S_2Cu$ | 597.5 | m.p. > 300° C | 60 % | C: 48.20 / F: 48.16 | 5.02 / 5.10 | 9.37 / 9.23 | 10.62 / 10.49 |
| 3 | 2-Cl-phenyl | $C_{12}H_{15}ClN_2O_3S$ | 302.5 | m.p. 173° C | 79.6 % | C: 47.60 / F: 47.73 | 4.96 / 5.09 | 9.26 / 9.17 |  |
| 4 | 3-Cl-phenyl | $C_{12}H_{15}ClN_2O_3S$ | 302.5 | m.p. 129.2° C | 77.3 % | C: 47.60 / F: 47.60 | 4.96 / 4.98 | 9.26 / 9.23 |  |
| 5 | 4-Cl-phenyl | $C_{12}H_{15}ClN_2O_3S$ | 302.5 | m.p. 179° C | 75.8 % | C: 47.60 / F: 47.63 | 4.96 / 4.99 | 9.26 / 9.23 |  |
| 6 | 2,6-Cl$_2$-phenyl | $C_{12}H_{14}Cl_2N_2O_3S$ | 337 | m.p. 163° C | 90 % | C: 42.73 / F: 42.65 | 4.15 / 4.13 | 8.31 / 8.26 |  |
| 7 | 2,4-Cl$_2$-phenyl | $C_{12}H_{14}Cl_2N_2O_3S$ | 337 | m.p. 175° C | 80.4 % | C: 42.73 / F: 42.80 | 4.15 / 4.18 | 8.31 / 8.28 |  |
| 8 | 2,5-Cl$_2$-phenyl | $C_{12}H_{14}Cl_2N_2O_3S$ | 337 | m.p. 174° C | 94 % | C: 42.73 / F: 42.56 | 4.15 / 4.09 | 8.31 / 8.27 |  |
| 9 | 2,3-Cl$_2$-phenyl | $C_{12}H_{14}Cl_2N_2O_3S$ | 337 | m.p. 156.3° C | 83 % | C: 42.73 / F: 42.70 | 4.15 / 4.17 | 8.31 / 8.33 |  |
| 10 | 3,4-Cl$_2$-phenyl | $C_{12}H_{14}Cl_2N_2O_3S$ | 337 | m.p. 164.1° C | 92.5 % | C: 42.73 / F: 42.89 | 4.15 / 4.20 | 8.31 / 8.32 |  |
| 11 | 3,5-Cl$_2$-phenyl — Cu (II) salt | $C_{12}H_{14}Cl_2N_2O_3S$ | 337 | m.p. 178.2° C | 83.2 % | C: 42.73 / F: 42.40 | 4.15 / 4.15 | 8.31 / 8.40 |  |

-continued $$R-NH-CO-NH-\underset{\underset{COOH}{|}}{CH}-CH_2CH_2SCH_3$$

| Compound No. | R | Structure obtained | | | | | | |
|---|---|---|---|---|---|---|---|---|
| | | Empirical formula | MW | Physical constants | Yield | Centesimal analysis | | |
| 12 | 3,4-diCl-phenyl | $C_{24}H_{26}Cl_4N_4O_6S_2Cu$ | 735.5 | m.p. > 300° C | 93 % | C: 39.15 F: 39.16 | 3.53 3.90 | 7.61 8.63 7.60 8.60 |
| 13 | 4-$O_2N$-phenyl | $C_{12}H_{15}N_3O_5S$ | 313 | m.p. 180.1° C | 59 % | C: 46.01 F: 45.97 | 4.79 4.92 | 13.42 13.19 |
| 14 | 4-NC-phenyl | $C_{13}H_{15}N_3O_3S$ | 293 | m.p. 163.1° C | 81.5 % | C: 53.24 F: 53.12 | 5.12 5.23 | 14.33 14.20 |
| 15 | 3-$CF_3$-phenyl | $C_{13}H_{15}F_3N_2O_3S$ | 336 | m.p. 153° C | 85 | C: 46.43 F: 46.40 | 4.46 4.37 | 8.33 8.28 |
| 16 | 2-$CH_3$-phenyl | $C_{13}H_{18}N_2O_3S$ | 282 | m.p. 156° C | 82.5 % | C: 55.32 F: 55.29 | 6.38 6.39 | 9.93 10.09 |
| 17 | 3-$CH_3$-phenyl | $C_{13}H_{18}N_2O_3S$ | 282 | m.p. 140.5° C | 83.6 % | C: 55.32 F: 55.38 | 6.38 5.96 | 9.93 10.0 |
| 18 | 4-$CH_3$-phenyl | $C_{13}H_{18}N_2O_3S$ | 282 | m.p. 155.10° C | 83.5 % | C: 55.32 F: 55.35 | 6.38 6.09 | 9.93 10.12 |
| 19 | 4-isopropyl-phenyl | $C_{15}H_{22}N_2O_3S$ | 310 | m.p. 135.1° C | 86.2 % | C: 58.06 F: 58.08 | 7.10 7.09 | 9.03 9.08 |
| 20 | 4-t-butyl-phenyl | $C_{16}H_{24}N_2O_3S$ | 324 | m.p. 149.5° C | 78.5 % | C: 59.26 F: 59.33 | 7.41 7.39 | 8.64 8.70 |
| 21 | 4-$CH_3O$-phenyl | $C_{13}H_{18}N_2O_4S$ | 298 | m.p. 174° C | 76.4 % | C: 52.35 F: 52.22 | 6.04 6.04 | 9.40 9.41 |
| 22 | naphthyl | $C_{16}H_{18}N_2O_3S$ | 318 | m.p. 140.5° C | 70 % | C: 60.38 F: 60.35 | 5.66 6.05 | 8.81 8.89 |
| 23 | phenyl-CH=CH- | $C_{14}H_{18}N_2O_3S$ | 294 | m.p. 136° C | 70 % | C: 57.14 F: 57.13 | 6.12 5.93 | 9.52 9.56 |
| 24 | 2,4-diCl-benzyl | $C_{13}H_{16}N_2O_3SCl_2$ | 351 | m.p. 145.8° C | 76 % | C: 44.44 F: 44.25 | 4.56 4.38 | 7.98 7.79 |
| 25 | cyclohexyl | $C_{12}H_{22}N_2O_3S$ | 274 | m.p. 142.7° C | 93.5 % | C: 52.55 F: 54.01 | 8.03 8.20 | 10.22 9.65 |
| 26 | H | $C_6H_{12}N_2O_3S$ | 192 | m.p. 143° C | 76.5 % | C: 37.50 F: 37.34 | 6.25 6.35 | 14.58 14.55 |

EXAMPLE 12

Preparation of the copper (II) salt of the compound of Example 11

The procedure is as in Example 2 using N-(3,5-dichlorphenyl)-N'-(1-carboxy-3-methyl thio)-propyl urea Yield: 23%

Melting point: above 300° C

Centesimal analysis for $C_{24}H_{26}Cl_4N_4O_6S_2Cu$

| % | C | H | N | Cu |
|---|---|---|---|---|
| calculated | 39.15 | 3.53 | 7.61 | 8.63 |
| found | 39.16 | 3.90 | 7.60 | 8.60 |

EXAMPLES 27 to 50

Preparation of compounds of formula (II), in which $R_2$ is hydrogen, by cyclising the starting urea.

EXAMPLE 27

Preparation of 3-phenyl-5-methylthioethyl hydantoin 268 g (1 mole) of compound no. 1 are boiled for a prolonged period in concentrated hydrochloric acid (21° Be). The hydantoin precipitates on cooling. It is centrifuged, washed with water and dried.

After recrystallisation from methanol, it melts at 110.5° C.

Yield: 86%

Centesimal analysis for $C_{12}H_{14}N_2O_2S$

| % | C | H | N |
|---|---|---|---|
| calculated | 57.60 | 5.60 | 10.20 |
| found | 57.64 | 5.68 | 10.22 |

EXAMPLES 28 to 50

The procedure is as in Example 27. The characteristics of the compounds obtained and their yields are set out in the following Table:

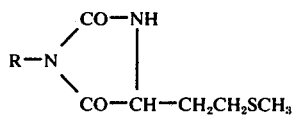

| Compound No. | R | Empirical formula | MW | Physical constants | Yield | Centesimal analysis | | |
|---|---|---|---|---|---|---|---|---|
| | | | | | | | C % | H % | N % |
| 27 | phenyl | $C_{12}H_{14}N_2O_2S$ | 250 | m.p. 110.5° C | 86 % | C: 57.60  F: 57.64 | 5.60  5.68 | 11.20  11.22 |
| 28 | 4-Cl-phenyl | $C_{12}H_{13}ClN_2O_2S$ | 284.5 | m.p. 137° C | 89.2 | C: 50.62  F: 50.95 | 4.57  4.56 | 9.84  10.07 |
| 29 | 3-Cl-phenyl | $C_{12}H_{13}ClN_2O_2S$ | 284.5 | m.p. 94.1° C | 90.7 % | C: 50.62  F: 50.59 | 4.57  4.61 | 9.84  9.84 |
| 30 | 4-Cl-phenyl | $C_{12}H_{13}ClN_2O_2S$ | 284.5 | m.p. 129° C | 89 % | C: 50.62  F: 50.62 | 4.57  4.62 | 9.84  9.83 |
| 31 | 2,6-diCl-phenyl | $C_{12}H_{12}Cl_2N_2O_2S$ | 319 | m.p. 121.5° C | 71 % | C: 45.14  F: 45.22 | 3.76  3.89 | 8.78  8.70 |
| 32 | 2,4-diCl-phenyl | $C_{12}H_{12}Cl_2N_2O_2S$ | 319 | m.p. 120° C | 83.5 % | C: 45.14  F: 45.13 | 3.76  4.04 | 8.78  8.68 |
| 33 | 2-Cl-phenyl | $C_{12}H_{12}Cl_2N_2O_2S$ | 319 | m.p. 117° C | 74 % | C: 45.14  F: 45.09 | 3.76  3.77 | 8.78  8.83 |
| 34 | 2,3-diCl-phenyl | $C_{12}H_{12}Cl_2N_2O_2S$ | 319 | m.p. 136° C | 60 % | C: 45.14  F: 44.99 | 3.76  3.68 | 8.78  8.73 |
| 35 | 3,4-diCl-phenyl | $C_{12}H_{12}Cl_2N_2O_2S$ | 319 | m.p. 109.2° C | 73.3 % | C: 45.14  F: 45.05 | 3.76  4.09 | 8.78  8.81 |
| 36 | 3,5-diCl-phenyl | $C_{12}H_{12}Cl_2N_2O_2S$ | 319 | m.p. 126° C | 78.5 % | C: 45.14  F: 45.08 | 3.76  3.82 | 8.78  8.84 |

-continued

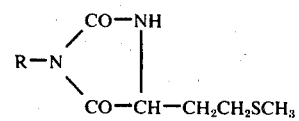

| Compound No. | R | Empirical formula | MW | Physical constants | Yield | Centesimal analysis | | |
|---|---|---|---|---|---|---|---|---|
| 37 | O₂N—⟨O⟩— | C₁₂H₁₃N₃O₄S | 295 | m.p. 153.4° C | 65 % | C: 48.81<br>F: 49.05 | 4.41<br>4.17 | 14.24<br>14.24 |
| 38 | HOOC—⟨O⟩— | C₁₃H₁₄N₂O₄S | 294 | m.p. 250° C | 53 % | C: 53.1<br>F: 53.26 | 4.76<br>4.93 | 9.52<br>9.53 |
| 39 | CF₃—⟨O⟩— | C₁₃H₁₃F₃N₂O₂S | 318 | m.p. 100° C | 76 % | C: 49.06<br>F: 48.97 | 4.09<br>4.05 | 8.81<br>8.75 |
| 40 | ⟨O⟩—CH₃ | C₁₃H₁₆N₂O₂S | 264 | m.p. 124° C | 83.4 % | C: 59.09<br>F: 59.17 | 6.06<br>6.08 | 10.61<br>10.58 |
| 41 | CH₃—⟨O⟩— | C₁₃H₁₆N₂O₂S | 264 | m.p. 97° C | 89.4 % | C: 59.09<br>F: 59.10 | 6.06<br>6.14 | 10.61<br>10.43 |
| 42 | CH₃—⟨O⟩— | C₁₃H₁₆N₂O₂S | 264 | m.p. 131°C | 85 % | C: 59.09<br>F: 59.26 | 6.06<br>5.73 | 10.61<br>10.50 |
| 43 | (CH₃)₂CH—⟨O⟩— | C₁₅H₂₀N₂O₂S | 292 | m.p. 127.4° C | 77 % | C: 61.64<br>F: 61.58 | 6.85<br>6.86 | 9.59<br>9.59 |
| 44 | (CH₃)₃C—⟨O⟩— | C₁₆H₂₂N₂O₂S | 306 | m.p. 149.3° C | 85.7 % | C: 62.75<br>F: 62.88 | 7.19<br>7.01 | 9.15<br>9.16 |
| 45 | CH₃O—⟨O⟩— | C₁₃H₁₆N₂O₃S | 280 | m.p. 128.10 | 85 % | C: 55.71<br>F: 55.67 | 5.71<br>5.76 | 10.00<br>10.02 |
| 46 | naphthyl | C₁₆H₁₆N₂O₂S | 300 | m.p. 121° C | 73 % | C: 64.0<br>F: 64.09 | 5.33<br>5.30 | 9.33<br>9.22 |
| 47 | CH₃— | C₇H₁₂N₂O₂S | 188 | m.p. 104° C | 90.5 % | C: 44.68<br>F: 44.71 | 6.38<br>6.42 | 14.89<br>14.89 |
| 48 | Cl—⟨O⟩(Cl)—CH₂— | C₁₃H₁₄N₂O₂Cl₂S | 333 | m.p. 154.6° C | 86 % | C: 46.85<br>F: 46.90 | 4.20<br>4.23 | 8.41<br>8.38 |
| 49 | cyclohexyl | C₁₂H₂₀N₂O₂S | 256 | m.p. 110.8° C | 74 % | C: 56.25<br>F: 56.26 | 7.81<br>7.79 | 10.94<br>10.80 |
| 50 | H | C₆H₁₀N₂O₂S | 174 | m.p. 105° C | 41.3 % | C: 41.34<br>F: 41.15 | 5.75<br>5.73 | 16.09<br>15.91 |

EXAMPLE 51

Preparation of 3-carboxyethyl-5-methylthioethyl hydantoin 189 g (1 mole) of the isocyanate derivative of the methyl ester of dl-methionine are poured slowly into a pyridine solution of β-alanine (89 g, 1 mole). The reaction takes place spontaneously, accompanied by the elimination of methanol. The reaction medium is then concentrated to dryness under reduced pressure. The residue is purified by recrystallisation from dichlorethane.

Yield: 89%
Melting point: 113° C
Centesimal analysis for $C_9H_{14}N_2O_4S$

| % | C | H | N | S |
|---|---|---|---|---|
| calculated | 43.80 | 5.68 | 11.36 | 13.01 |
| found | 43.66 | 6.08 | 11.34 | 13.03 |

EXAMPLES 52 to 54

The procedure is as in the preceding Example, but using a suitable amine. The characteristics of the compounds obtained and their yields are set out in the following Table:

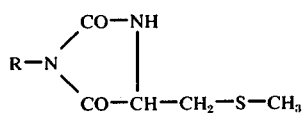

| Compound No. | R | Empirical formula | MW | Physical constants | Yield | Centesimal analysis | | |
|---|---|---|---|---|---|---|---|---|
| | | | | | | C % | H % | N % |
| 52 | 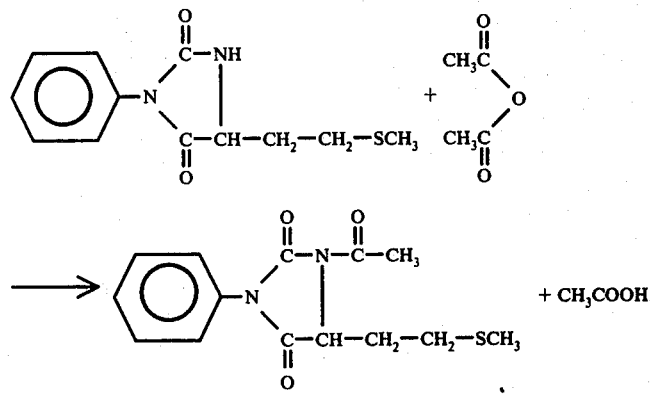-CH₂- | $C_{11}H_{14}N_2O_3S$ | 254 | m.p. 103.7° C | 39.5 % | C: 51.97<br>F: 52.12 | 5.51<br>5.13 | 11.02<br>10.99 |
| 53 | | $C_{11}H_{13}N_3O_2S$ | 251 | m.p. 140.2° C | 72 % | C: 52.59<br>F: 52.59 | 5.18<br>5.19 | 16.73<br>16.70 |
| 54 | | $C_{11}H_{13}N_3O_2S$ | 251 | m.p. 157.3° C | 62.5 % | C: 52.59<br>F: 52.80 | 5.18<br>5.00 | 16.73<br>16.79 |

EXAMPLE 55

Preparation of 1-methyl-3-phenyl-5-(methylthioethyl)-hydantoin

A solution in acetone of 250 g (1 mole) of 3-phenyl-5-methylthioethyl hydantoin (compound no. 27) and 126 g (1 mole) of methyl sulphate is heated under reflux for 8 hours, accompanied by the addition with stirring of 138 g (1 mole) of potassium carbonate. The concentration of the acetone solution is between 0.5 and 1 mole per liter. On completion of the reaction, the potassium salts are separated by filtration and the acetone eliminated by evaporation. The residue crystallises on cooling. It can be recrystallised from methanol.
Yield: 55%
Melting point: 68° C
Centesimal analysis for $C_{13}H_{16}N_2O_2S$

| % | C | H | N |
|---|---|---|---|
| calculated | 59.09 | 6.06 | 10.60 |
| found | 59.07 | 6.05 | 10.67 |

EXAMPLE 56

Preparation of 1-acetyl-3-phenyl-5-(methylthioethyl)-hydantoin

A mixture of 250 g (1 mole) of compound no. 27, 500 cc of acetic anhydride and 25 g of molten sodium acetate is heated under reflux for 3 hours. After evaporation of the volatile fraction, the residue is taken up in water. The crystals are recrystallised from dilute ethanol. The reaction scheme is as follows:

Yield: 91%
Melting point: 84° C
Centesimal analysis for $C_{14}H_{16}N_2O_3S$

| % | C | H | N |
|---|---|---|---|
| calculated | 57.53 | 5.47 | 9.58 |
| found | 57.53 | 5.49 | 9.63 |

EXAMPLE 57

Preparation of 1-(β-chlorethoxycarbonyl)-3-phenyl-5-(methylthioethyl)-hydantoin 143 g (1 mole) of β-chlorethyl chloroformate are added dropwise to a solution in chloroform of 250 g (1 mole) of compound no. 27 and 101 g (1 mole) of triethylamine (TEA). The concentration of the medium is approximately 1 mole per liter. The reaction is continued by heating under reflux for 5 hours. After washing the organic fraction with water, the solvent is evaporated under reduced pressure. The title compound is isolated by fractional crystallisation in methanol:

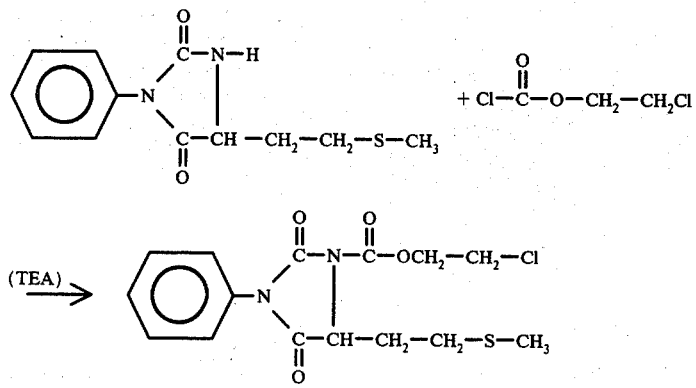

Yield: 78%
Melting point: 104° C
Centesimal analysis for $C_{15}H_{17}ClN_2O_4S$

| % | C | H | N | Cl |
|---|---|---|---|---|
| calculated | 50.51 | 4.77 | 7.85 | 9.95 |
| found | 50.54 | 4.83 | 7.86 | 9.98 |

EXAMPLE 58

Preparation of 1-(n-propylcarbamoyl)-3-phenyl-5-(methylthioethyl)-hydantoin 125 g of compound no. 27 (0.5 mole), 42.5 g of propylisocyanate (0.5 mole) and 50 g of TEA (0.5 mole), all being dissolved in anhydrous acetone, are heated under reflux for several hours.

On completion of the reaction, the solvents are eliminated under reduced pressure and the residue recrystallised from methanol.

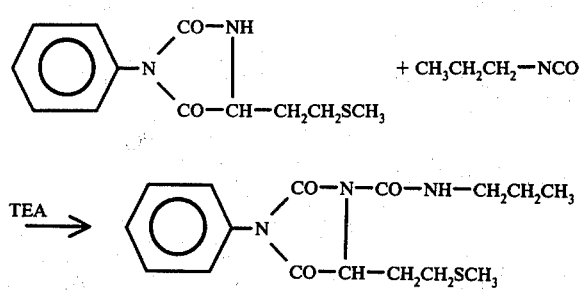

Yield: 86.5%
Melting point: 84° C
Centesimal analysis for $C_{16}H_{21}N_3O_3S$

| | C % | H % | N % | S % |
|---|---|---|---|---|
| calculated | 57.31 | 6.27 | 12.54 | 9.55 |
| found | 57.35 | 6.22 | 12.52 | 9.57 |

EXAMPLE 59

Preparation of dimethyl-(3-phenylhydantoinyl)-ethyl-sulphonium iodide 250 g (1 mole) of compound no. 27 and 142 g (1 mole) of methyl iodide in solution in anhydrous acetone are mixed with stirring at room temperature. The sulphonium salt precipitates after 5 hours. It is centrifuged, washed and dried.

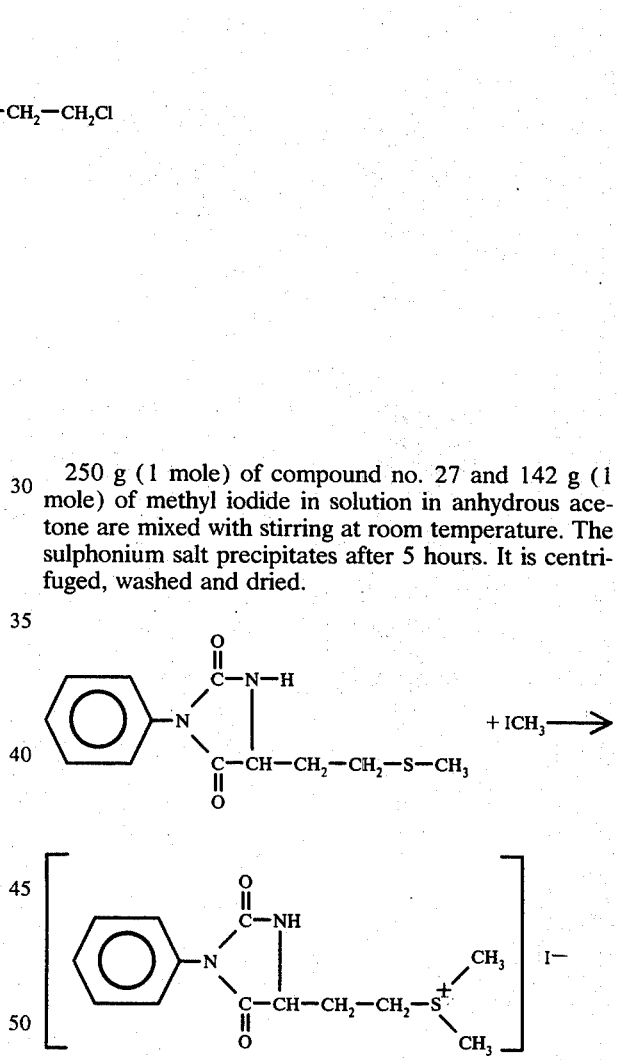

Yield: 87%
Melting point: 130° C
Centesimal analysis for $C_{13}H_{17}IN_2O_2S$

| % | C | H | N |
|---|---|---|---|
| calculated | 39.80 | 4.33 | 7.15 |
| found | 39.66 | 4.33 | 7.12 |

EXAMPLES 60 to 62

The procedure is as in the preceding Example, varying either the hydantoin or the methyl halide or both. The characteristics of the compounds obtained and their yields are set out in the following Table:

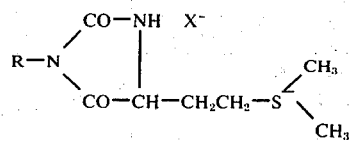

| Compound No. | R | X⁻ | Empirical formula | Physical constants | Yield | Centesimal analysis ||||||
|---|---|---|---|---|---|---|---|---|---|---|---|
| | | | | | | | C % || H % || N % |
| 60 | phenyl | Br⁻ | $C_{13}H_{17}BrN_2O_2S$ | m.p. 155.9 | 40.6 % | C: | 45.22 | | 4.93 | | 8.12 |
| | | | | | | F: | 45.36 | | 4.98 | | 8.16 |
| 61 | 2,4-Cl₂-phenyl | I⁻ | $C_{13}H_{15}Cl_2IN_2O_2S$ | m.p. 117.5° C | 42 % | C: | 39.9 | | 3.26 | | 6.07 |
| | | | | | | F: | 35.32 | | 3.58 | | 5.98 |
| 62 | 3,4-Cl₂-phenyl | Br⁻ | $C_{13}H_{15}BrCl_2N_2O_2S$ | m.p. 153.8° C | 19.6 % | C: | 37.68 | | 3.62 | | 6.76 |
| | | | | | | F: | 38.21 | | 4.06 | | 6.88 |

EXAMPLE 63

Preparation of N-methyl, N' (I-cyano, 3 methylthio) propylurea

A solution of 2,85 g (0;05 mole) of methylisocyanate in benzene is added dropwise to a solution of 0,5 g (0,05 mole) of 2-amino 4-buryronitrile. The temperature is maintained under 30° C during this time. After half an hour of contact, the desired compound begins to precipitate. When it is completely cooled, it is centrifugated, washed and dried. It is then recrystallised in ethyl acetate.

Yield: 84%
Melting point: 107° C
Centesimal analysis for $C_7H_{13}N_3$ OS

| | C % | H % | N % |
|---|---|---|---|
| Calculated | 44,91 | 6,96 | 22,45 |
| Found | 44,05 | 6,98 | 22,40 |

EXAMPLES 64 to 67

The procedure is the same as the preceding example, but using a suitable isocyanate. The characteristics of the compounds obtained and their yields are set out in the following table:

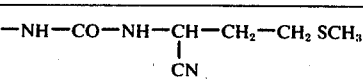

| Compound No. | R | Empirical formula | MW | Physical constants | Yield | Centesimal analysis ||||||
|---|---|---|---|---|---|---|---|---|---|---|---|
| | | | | | | | C % || H % || N % |
| 63 | $CH_3-$ | $C_7H_{13}N_3OS$ | 187 | m.p. 107° C | 83.5 % | C: | 44.91 | | 6.96 | | 22.45 |
| | | | | | | F: | 45.05 | | 6.98 | | 22.40 |
| 64 | phenyl | $C_{12}H_{15}N_3OS$ | 249 | m.p. 114.5° C | 77 % | C: | 57.83 | | 6.02 | | 16.87 |
| | | | | | | F: | 57.58 | | 6.10 | | 16.69 |
| 65 | 2,4-Cl₂-phenyl | $C_{12}H_{13}Cl_2N_3OS$ | 318 | m.p. 119° C | 79 % | C: | 45.28 | | 4.09 | | 13.21 |
| | | | | | | F: | 45.14 | | 4.17 | | 13.19 |
| 66 | 3,4-Cl₂-phenyl | $C_{12}H_{13}Cl_2N_3OS$ | 318 | 134.5° C | 69 % | C: | 45.28 | | 4.09 | | 13.21 |
| | | | | | | F: | 45.12 | | 4.12 | | 13.47 |
| 67 | naphthyl | $C_{16}H_{17}N_3OS$ | 299 | m.p. 131° C | 74.5 % | C: | 64.21 | | 5.69 | | 14.05 |
| | | | | | | F: | 64.28 | | 5.74 | | 14.41 |

The biological properties of the compounds according to the invention were demonstrated by tests in which the plants or seeds were treated by various methods depending essentially upon the type of plants tested and by the expected responses.

The term "solution" as used in the following relates either to an aqueous solution, where the active material is soluble in water, or, in the opposite case, an aqueous dispersion of a wettable powder containing 20% of the active material.

In a first method, so-called root treatment, applicable to peas, 2 to 6 day old seedlings of two varieties, one dwarf "Petit Provencal", the other giant "Alaska", are placed on the surface of a solution containing from 1 to 10 g/l of the material to be tested in such a way that their roots are immersed. After 3 to 5 days, the biometric and morphological development of the seedlings is observed and recorded.

For other plants, such as French beans, tomatoes, maize, cotton, sunflower, gherkin, chrysanthemum, at the 2 to 4 leaf stage, and also for fruit trees, pineapples, etc., the leaves are treated by spraying with a solution containing 1 to 10 g/l of the material to be tested. The biometric and morphological development of the plants is then noted after 8 days, 25 days, 1 month and even after 6 months in certain cases, such as the fruit trees.

It is also possible, in the case of such plants as maize, tomato, tobacco, cotton, barley, peas, mustard, to immerse seeds of these plants for 24 hours in a solution containing 1 to 10 g/l of the material to be tested. The treated seeds are then sown. The biometric and morphological development of the plants is then noted.

For most of the tests on barley, the seeds of this plant are germinated on the surface of a solution containing 1 to 10 g/l of the material to be tested. The biometric and morphological development of the seedlings is noted after 3 and 5 days.

Finally, in certain fruit-ripening tests, size-controlled green fruit collected at one and the same level of the plant is immersed for 24 hours in a solution of the material to be tested in concentrations ranging from 1 to 10 g/l. The progress of external and internal ripening of the fruit is noted.

Several modes of action of the compounds according to the invention on the growth of the aforementioned plants are studied in the following Examples using these methods.

EXAMPLE I

Reduction in size

The size of epicotyles and the node intervals of treated species are measured in relation to the controls.

Under these conditions, compounds 1, 18, 20, 26, 27, 51, 54, 55, 61 and 62 produce a reduction in growth of 16 to 45 % in a dose of 1 g/l for peas and barley and in a dose of 5 g/l for maize, sunflowers, cotton, French beans, and tomatoes, whilst dl-methionine has no effect on these plants.

EXAMPLE II

Modification of the development of lateral shoots

Control is carried out by counting the number of lateral shoots and measuring their length over a period of time.

Under these conditions, it is found that, in dose of from 1 to 10 g/l,
compounds 1, 5, 10, 11, 27, 29, 30, 35, 43, 47 and 59 produce an increase in branching and a significant development of lateral shoots in tomato plants, bean plants and chrysanthemums;
compounds 17, 20, 21, 41, 42, 52, 55 and 56 retard the development of lateral shoots.

EXAMPLE III

Abscission of leaves

Control is carried out by counting the number of fallen leaves to assess the activity of the active materials in accelerating the dropping of leaves.

Under these conditions, it is found that
in a dose of 10 g/l, compounds 17, 29, 46, 47, 56, 57 and 60 produce a 50 to 80% abscission of leaves in bean plants;
in doses ranging from 1.2 to 5 kg/ha, compounds 27, 35 and 46 produce a 77 to 90% abscission of leaves in cotton.

These results were obtained in the open. dl-Methionine does not produce any abscission.

EXAMPLE IV

Action on the ripening and colouring of fruit

Green fruit from the Jerusalem cherry tree (*Solanum pseudocapsicum*) is immersed, on the one hand, in the products to be tested, and, on the other hand, in a known commparison compound: methionine, a control being reserved for comparison purposes.

After immersion, the fruit is placed in transparent containers with $CO_2$ absorbers kept under glass.

Under these conditions, it is found that, whereas the controls ripen in 12 days, the fruit treated with methionine ripens in 10 days and the fruit treated with compounds 1, 5, 10, 27 and 37 in 3 days.

In open-air tests on pineapples, in which treatment was carried out by spraying, compounds 11, 27, 35 and 46 were found to accelerate ripening which made it possible to reorganise gathering and to reduce the time involved from 12 to 6 days.

EXAMPLE V

Action on flowering and fructification

Control was carried out by noting the number of flowers and/or fruit of the treated plants in relation to an untreated control. The delay or advance produced in flowering is also observed.

Under these conditions, it is found that
in a dose of 5 g/l, compounds 11 and 36 increase the harvest of beans by 100%;
in the same dose of 5 g/l, compounds 17, 18, 20 and 21 increase the number of fruit on bean plants by 20 to 50%;
in the same dose of 5 g/l, compounds 14, 17, 24, 25, 26, 37, 38, 46 and 49 retard flowering in beans and gherkins by 5 to 6 days;
in open-air tests, compounds 11, 27, 35 and 46 initiate flowering in pineapples.

EXAMPLE VI

Action on germination

The delay in the germination of treated seeds is noted in relation to that of untreated control seeds.

Under these conditions, it is found that compounds 5 and 47 inhibit the germination of 66% of maize seeds. This inhibition is temporary in a dose of 1 g/l and becomes definitive in a dose of 10 g/l.

EXAMPLE VII

Epinasty Effect

The deformation (twisting) produced in the stems of plants is observed. Under these conditions, it is found that, in a dose of 10 g/l, compound no. 44 produces marked deformation in peas treated through their roots.

EXAMPLE VIII

Action on the colouring of leaves

The greenness of leaves during treatment by spraying is compared with that of new leaves produced by lateral shoots.

Under these conditions, it is found that compounds 4, 5, 10, 22, 24, 25, 26, 29, 30, 35, 46, 47, 48, 49, 56 and 57 provide the new leaves of bean and tomato plants with a deep green colour. This is confirmed by the dosage of chlorophyl, of which the quantity was doubled in the leaves treated with the above compounds.

Further, open air trials have shown that some compounds according to the invention when used on cotton increase the number of capsules up to 50 % and floral induction up to 40 %. Other compounds have been found very effective to get a gathered fall of olives which facilitates the gathering very much.

These Examples clearly demonstrate the remarkable properties of the compounds according to the invention which can thus be used in any type of plant, for example in largescale cultivation, intensive cultivation, in cereals, fruits, vegetables, ornamental plants, medicinal plants and perfume plants with a view to increasing productivity, facilitating harvest, for example by abscission of leaves, accelerating the ripening of fruit, promoting branching, modifying habit, producing floral induction (flowering), retarding flowering to prevent frost damage, reducing size to obtain more compact plants, etc.

The doses in which the compounds according to the invention can be used vary within wide limits depending upon the required effect, upon the type of plant and its stage of treatment, upon the soil and climatic conditions. In general, doses of from 0.1 to 10 g/l are adequate.

In practice, the compounds according to the invention are rarely used on their own. More often, they are an integral part of formulations which generally comprise a support and/or a surfactant in addition to the active material according to the invention.

In the context of the invention, a support is an organic or mineral, natural or synthetic material with which the active material is associated to facilitate its application to the plant, to seeds or to soil, or its transportation or handling. The support can be solid (clays, natural or synthetic silicates, resins, waxes, solid fertilisers) or fluid (water, alcohols, ketones, petroleum fractions, chlorinated hydrocarbons, liquefied gases).

The surfactant can be an ionic or non-ionic emulsifier, dispersant or wetting agent such as, for example, salts of polyacrylic acids and lignin-sulphonic acids, condensates of ethylene oxide with fatty alcohols, fatty acids or fatty amines.

The compositions according to the invention can be prepared in the form of wettable powders, powders for dusting, granulates, solutions, emulsifiable concentrates, emulsions, suspended concentrates and aerosols.

The wettable powders according to the invention can be prepared in such a way that they contain from 20 to 95% by weight of active material, and they normally contain, in addition to a solid support, from 0 to 5% of a wetting agent, from 3 to 10% by weight of a dispersant and, when necessary, from 0 to 10% by weight of one or more stabilisers and/or other additives, such as penetration agents, adhesives or anti-lumping agents, colorants, etc.

One example of the composition of a wettable powder is given below, the percentages being expressed in weight:

| | |
|---|---|
| active material | 50 % |
| calcium lignosulphate (deflocculant) | 5 % |
| isopropylnaphthalene sulfonate (wetting agent) | 1 % |
| anti-lumping silica | 5 % |
| filler (kaolin) | 39 % |

The emulsifiable concentrates which can be applied by spraying generally contain, in addition to the solvent and, when necessary, a co-solvent, from 10 to 50% by weight/volume of active material, from 2 to 20% by weight/volume of suitable additives, such as stabilisers, penetration agents, corrosion inhibitors, colorants and adhesives.

The suspended concentrates which can also be applied by spraying are prepared in such a way that a fluid, stable non-sedimenting product is obtained, and they normally contain from 10 to 75% by weight of active material, from 0.5 to 15% by weight of surfactants, from 0.1 to 10% by weight of anti-sedimentation agents, such as protective colloids and thixotropic agents, from 0 to 10% by weight of suitable additives, such as antifoam agents, corrosion inhibitors, stabilizers, penetration agents and adhesives, and as a support water or an organic liquid in which the active material is substantially insoluble. Certain solid organic materials or mineral salts can be dissolved in the support to assist in preventing sedimentation or as antifreeze agents for water.

Aqueous dispersions and emulsions, for example compositions obtained by diluting a wettable powder or an emulsifiable concentrate according to the invention with water, are included within the general scope of the invention. These emulsions can be of the water-in-oil type or of the oil-in-water type, and can have a thick consistency resembling that of a "mayonnaise".

The compositions according to the invention can contain other ingredients, for example protective colloids, adhesives or thickeners, thixotropic agents, stabilisers or sequestrants, and other active materials known to exhibit pesticidal properties, in particular insecticides, fungicides or growth regulators.

All these compositions can be applied to the plants by various methods, such as by spraying onto the aerial part of the plants, by soaking seeds, plants, clods, roots or fruit, by spraying the soil, by injecting the plant, etc.

We claim:

1. A composition for plant-growth regulation comprising an inert agricultural carrier and a plant-growth regulating effective amount of active compound of the formula

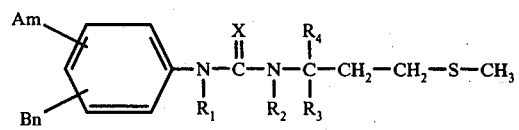

or is a salt thereof, wherein A is H or chlorine; B is H, chlorine, NO₂, CN, CF₃ or alkoxy or alkyl of 1–5 carbons; $m$ is 0 to 5; $n$ is 0 to 3; and $m + n$ is not greater than 5;

$R_1$, $R_2$ and $R_3$ which may be the same or different, represent hydrogen, or a $C_1 - C_5$ - alkyl radical;

$R_4$ is the carboxylic acid radical or a salt of an alkali metal, alkaline-earth metal or copper;

X represents oxygen or sulphur.

2. A composition in accordance with claim 1, wherein $R_1$, $R_2$ and $R_3$ all are hydrogen and $R_4$ is COOH.

3. A process for modifying the growth of plants wherein the plants are treated with a composition in accordance with claim 2.

4. A process for modifying the growth of plants wherein the plants are treated with a composition in accordance with claim 1.

5. A composition in accordance with claim 1, wherein $R_1$, $R_2$ and $R_3$ are all hydrogen; X is oxygen and $R_4$ is COOH.

6. A composition in accordance with claim 5, wherein Am and Bn are both Cl.

7. A composition in accordance with claim 6, wherein said active compound has the formula

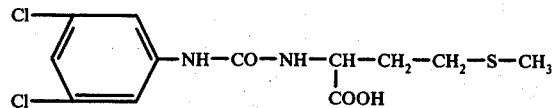

8. A composition in accordance with claim 6, wherein said active compound has the formula

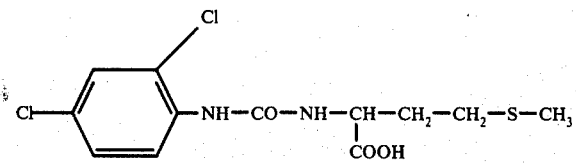

9. A composition in accordance with claim 1 wherein $R_1$ and $R_3$ are hydrogen, and $R_4$ is COOH.

10. A composition in accordance with claim 9 wherein A is halogen.

11. A composition in accordance with claim 1 further comprising a surfactant.

12. A method of regulating the growth of a plant comprising applying to said plant a plant-growth regulating effective amount of a compound of the formula

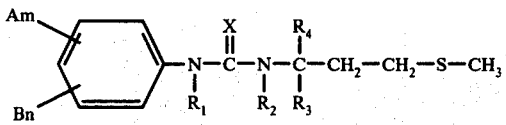

or is a salt thereof, wherein A is H or chlorine; B is H, chlorine, $NO_2$, CH, $CF_3$ or alkoxy or alkyl of 1-5 carbons;

$m$ is 0 to 5; $n$ is 0 to 3; and $m + n$ is not greater than 5;

$R_1$, $R_2$ and $R_3$, which may be the same or different, are hydrogen or a $C_1 - C_5$ — alkyl;

$R_4$ is the carboxylic acid radical or a salt of an alkali metal, alkaline-earth or copper; and X is O or S.

13. A composition in accordance with claim 1, wherein said active compound is the copper (II) salt of dl - N-phenyl-N'-(1-carboxy-3-methyl thio)-propyl urea.

14. A composition in accordance with claim 1, wherein said active compound is dl-N-(3-trifluoromethylphenyl)-N'-(1-carboxy-3-methyl-thio)-propyl urea.

* * * * *